United States Patent [19]

Bennett et al.

[11] Patent Number: 4,659,327

[45] Date of Patent: Apr. 21, 1987

[54] MULTIPLE DOSAGE SYRINGE

[75] Inventors: Douglas D. Bennett, Cambridge, Md.; Richard E. Welsh, Milford, Del.; Paul D. Hammesfahr, Dover, Del.; Earl C. Francis, Milford, Del.; Thomas V. Kopunek, Lewes, Del.

[73] Assignee: Dentsply Research & Development Corp., Milford, Del.

[21] Appl. No.: 801,974

[22] Filed: Nov. 26, 1985

[51] Int. Cl.$^4$ .............................................. A61M 5/20
[52] U.S. Cl. .................... 604/135; 604/209; 604/224; 401/66; 401/67; 222/391
[58] Field of Search ............... 604/135, 208, 209, 224; 401/65–67; 222/391, 386; 74/128, 141.5

[56] References Cited

U.S. PATENT DOCUMENTS

| | | |
|---|---|---|
| 1,718,596 | 6/1929 | Smith . |
| 2,120,625 | 6/1938 | Peckenpaugh ...................... 74/141.5 |
| 2,221,739 | 11/1940 | Reiter ................................... 604/135 |
| 2,472,116 | 6/1949 | Maynes ................................ 604/224 |
| 2,475,939 | 7/1949 | Applezweig ......................... 604/224 |
| 2,875,761 | 3/1959 | Helmer et al. . |
| 3,110,310 | 11/1963 | Cislak ................................... 604/209 |
| 3,141,583 | 7/1964 | Mapel et al. . |
| 3,334,788 | 8/1967 | Hamilton ............................ 604/135 |
| 3,517,668 | 6/1970 | Brickson . |
| 4,391,590 | 7/1983 | Dougherty . |

Primary Examiner—C. Fred Rosenbaum
Assistant Examiner—Mark Rooney
Attorney, Agent, or Firm—C. Hercus Just; Edward J. Hanson, Jr.

[57] ABSTRACT

A multiple, metered dosage device having an elongated body provided adjacent one end with a compartment or an ampule to contain material to be dispensed, a piston movable against the material to discharge it from a nozzle, a rod-like plunger movable by a pressure device against the piston to discharge material and a combination stop and release unit movable intermediately of the ends of the body between depressed and elevated positions respectively to engage a pair of racks of teeth on the plunger and including first and second teeth respectively engageable with the racks of teeth sequentially to permit the pressure device to advance the plunger and piston in similar metered, precise or predetermined increments of feeding in discharge direction and then stop the feeding movement and maintain such stopped position until the stop and release unit next is depressed.

4 Claims, 7 Drawing Figures

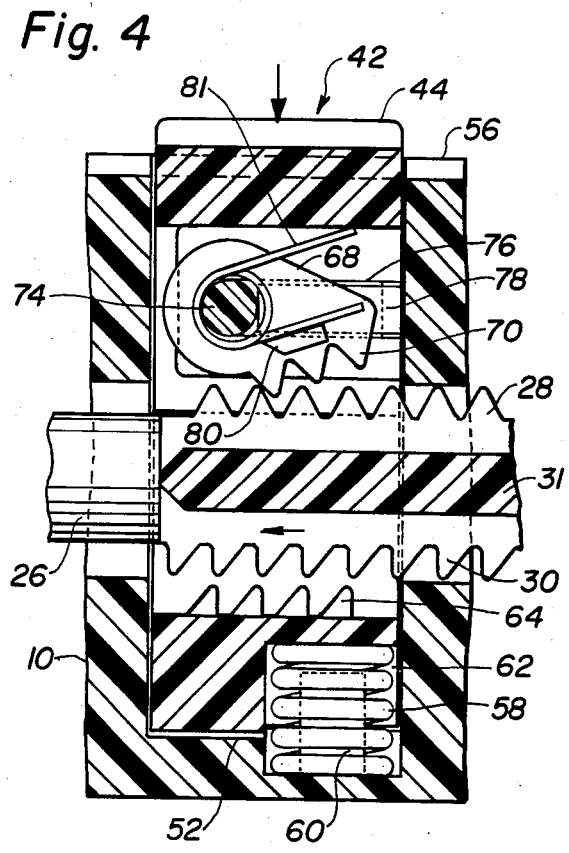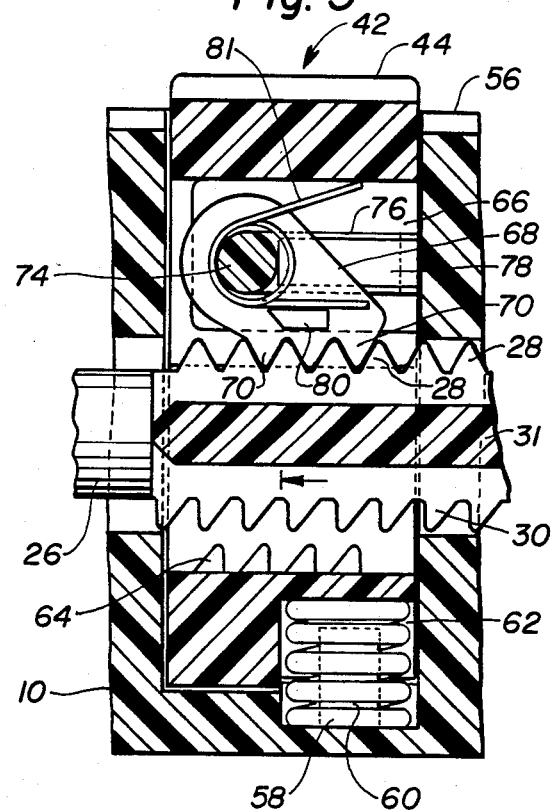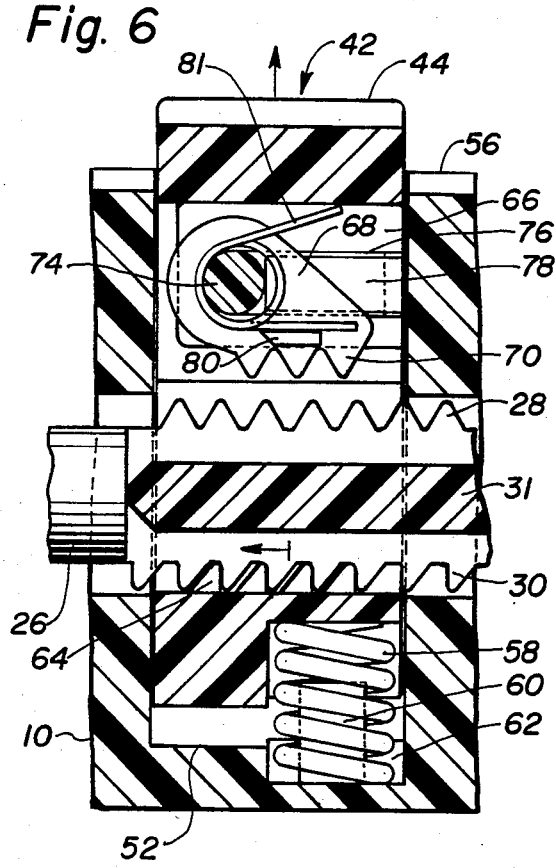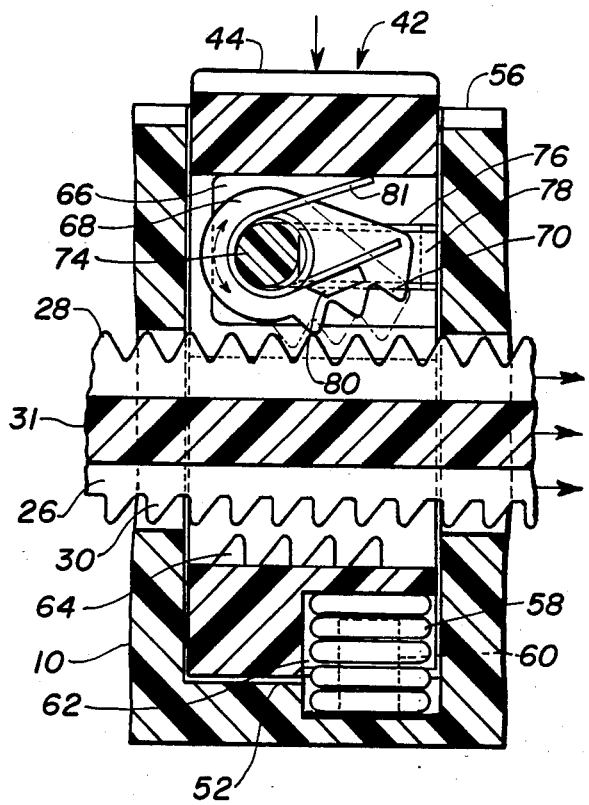

MULTIPLE DOSAGE SYRINGE

BACKGROUND OF THE INVENTION

In various medical fields and particularly in dentistry, it is desirable and often necessary to dispense materials into a prepared cavity or a crevice in relatively small but controlled increments or units of a product. This is particularly desired relative to the delivery of dental sealant materials, but also applies to certain other materials such as cements, adhesives, coating agents and the like. The present invention is directed to a syringe-like dispensing device capable of discharging relatively small metered quantities of material to a desired location for use and quickly repeating such discharges, if desired, until a sufficient amount has been applied where it is needed. The device of the present invention provides a means to deliver successive unit doses of cement, adhesives, pit and fissure sealants, filling materials and similar medical materials directly to the site in vivo.

Previous attempts have been made to discharge successive amounts of materials of various kinds by means of a syringe and certain syringes of a reasonably complex type have been developed and comprise the subject matter of the following U.S. Pats.:

U.S. Pat. No. 1,718,596—Smith, June 25, 1929
U.S. Pat. No. 141,583—Mapel et al., July 21, 1964
U.S. Pat. No. 3,517,668—Drickson, June 30, 1970

The syringes illustrated in said patents are of what is generally known as the pistol-grip type of syringe and include a lever movable relative to a handle and, in general, driving a piston rod having notches or teeth which are engaged by suitable advancing means actuated by the pivoted lever when moving toward and from said handle. In these devices, it also will be noted that a separate syringe having a movable piston therein is inserted within a compartment in the forward end of the barrels of the syringes. It also is to be noted that these prior devices lack precise control of the placement of the material in metered, pre-measured amounts, especially in small amounts.

A more simple type of multiple dosage syringe comprises the subject matter of prior U.S. Pat. No. 2,875,761 Helmer et al., dated Mar. 3, 1959. In this syringe, a plunger within the barrel of the syringe is actuated by an elongated member having a series of spaced notches therein which are capable of being engaged by a flexible stop member; the stop member riding along a smooth surface on the member until a subsequent notch is reached, at which time the flexible member drops into the notch and stops further feeding movement of the plunger.

The present invention, while not restricted thereto, primarily has been designed to support at the outer, delivery end thereof, a disposable, predosed ampule, syringe or cartridge such as that comprising the subject matter of prior U.S. Pat. No. 4,391,590 to Dougherty, patented July 5, 1983; but the invention is not particularly restricted to the employment of that specific cartridge or compule, details of such syringe being set forth below. Essentially, the invention dispenses material in metered, uniform doses or amounts which are clearly visible to the operator and such dispensing occurs by finger action of a control member which in no way is fatiguing due to minimum energy being required.

SUMMARY OF THE INVENTION

It is among the principle objects of the present invention to provide a relatively simple, easily actuated multiple dosage device, comprising an elongated body member having at the feeding or discharge end thereof, either a compartment to contain material to be dispensed or discharged or have means to support adjacent the discharge end, a predosed ampule, syringe or cartridge, one suitable example of which is illustrated in said aforementioned prior U.S. Pat. No. 4,391,590, which contains such material; the elongated body member having a rod-like feed member supported longitudinally therein and including spring or other pressure means arranged to normally urge or bias the feed means in forward, feeding direction; and the forward feeding movement of said feed member being controlled by a transversely reciprocable stop and release unit which effects successive, single increments of movement, which movement is stopped at the end of each advancing step while said spring meanwhile is endeavoring to move the feed member in feeding direction. The forward feeding pressure force may be a compressed spring, air pressure or other equivalent means, if alternative means are desired.

Another object of the invention is to provide rows of rack teeth on the elongated feed member or rod, which rows of rack teeth successively are engaged by movement-stopping teeth in the combination unit intermittently following engagement of additional movement-advancing teeth also carried by the combination unit for engaging the opposite row of rack teeth and the configuration of the respective teeth produces the limited desired feeding movement of the feed member.

A further object of the invention is to provide said movement-controlling combination unit with a dog mounted in the unit for limited pivotal movement and having one or more teeth thereon adapted to engage one of said rows of rack teeth in a cam-like manner so as to effect limited increment of advance movements of the elongated feed member when the unit depressed, said depressing movement also disengages the stop teeth of the unit from engagement with the opposite row of rack teeth, whereby as the actuating unit is successively reciprocated, the elongated feed member is progressively advanced and stopped sequentially.

Still another object of the invention is to provide the optionally disposable, predosed ampule, syringe or cartridge with a piston movable within the compartment in which the material to be dispensed is contained, said piston being engaged by the forward end of the aforementioned elongated feed member, the movement of which is controlled by the combination unit which is successively depressed and released, and when released, additional pressure means are arranged to project the unit to its extended or projected position, at which time the movement-stopping teeth thereon engage teeth of the adjacent elongated rack which stops the advancing movement.

Details of the foregoing objects and of the invention are set forth in the following specification and illustrated in the accompanying drawings comprising a part thereof.

BRIEF DESCRIPTION OF THE DRAWINGS

FIG. 4 is a vertical sectional view similar to FIG. 3, but showing the actuating unit depressed sufficiently to disengage the holding teeth of the unit out of engagement with the rack teeth and also illustrating the plunger starting to move toward the left-hand end as seen in said Figure as indicated by the direction arrow included in the Figure.

FIG. 5 is a view similar to FIG. 4, but showing the pivoted stopping member in full engagement with the rack teeth on the plunger for purposes of stopping further movement of the plunger in feeding direction.

FIG. 6 is a sectional view similar to FIGS. 3-5, but showing the actuating unit in the elevated position as shown in FIG. 2, and in which position the movement stopping teeth of the unit are engaged with the lower rack of teeth on the plunger; said view also showing a coil spring in expanded position which causes movement of the unit in the direction of the arrow shown at the top thereof while restraining the plunger from moving in feeding direction as indicated on the small direction arrow shown on said plunger in the Figure.

FIG. 7 is a view similar to FIGS. 3—6, but in which the movement stopping teeth of the unit have released engagement with the lower rack of teeth, such as when it is desired to retract the plunger in the direction of the arrow shown thereon and in which position the pivoted dog of the advancing mechanism is cammed from effective engagement with the upper row of rack teeth on the plunger.

DETAILED DESCRIPTION OF THE PREFERRED EMBODIMENT OF THE INVENTION

Figure 1:
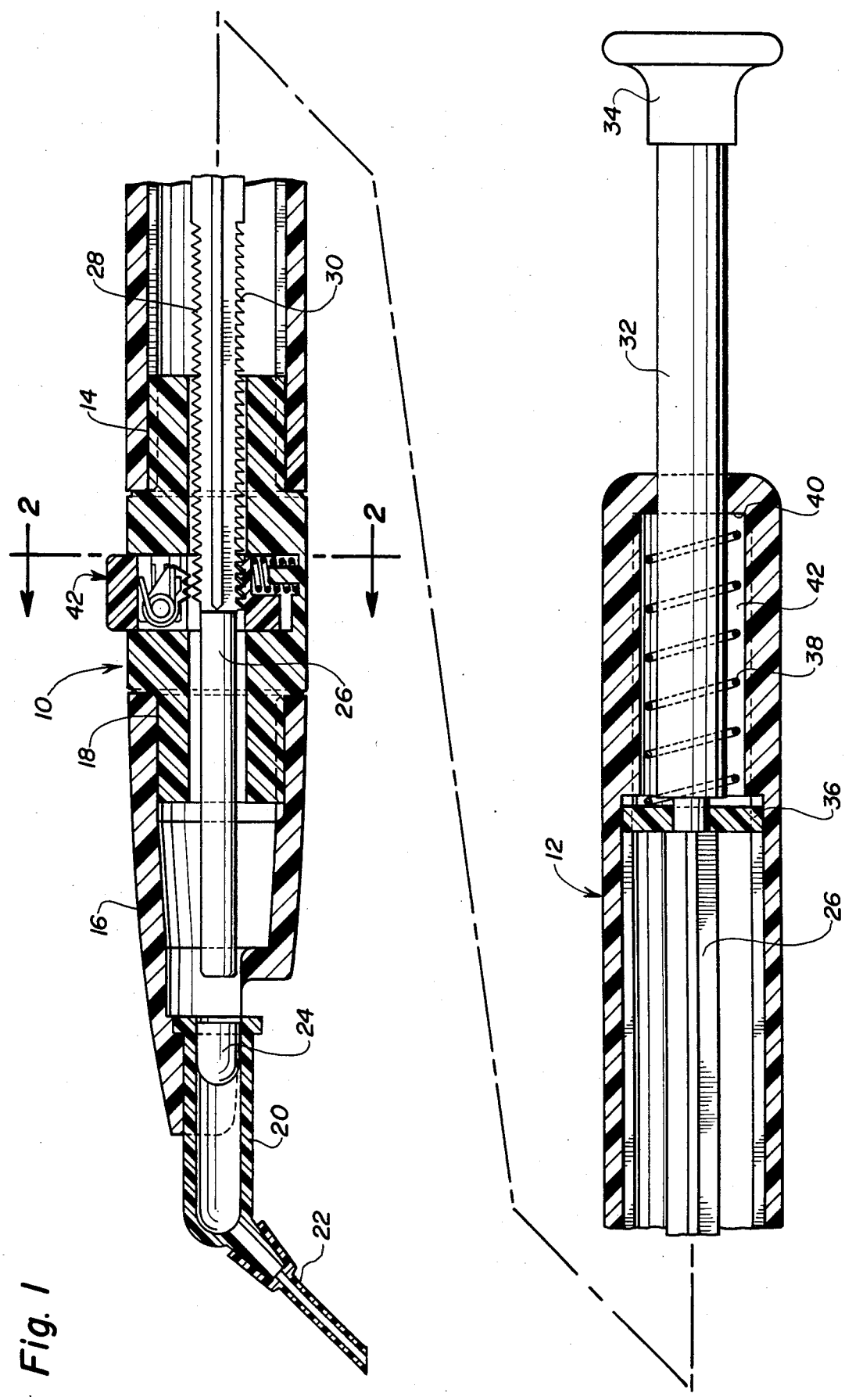
FIG. 1 is a two-part, fragmented vertical sectional view taken generally through the central area of the preferred embodiment of the syringe and showing the plunger in maximum retracted position.

Referring to the drawings, it will be seen that FIG. 1 is a fragmented illustration showing substantially the forward and rearward halves of the device in such fragmented manner for purposes of adapting the same to the sheet on a scale to render the components readily observable.

Essentially, the syringe comprises a bi-partite construction including a forward half 10 of a body and a rearward half 12 thereof, which are fixed together in telescoping manner as shown at the connection 14. Also, especially for purposes of ready assembly, forward half 10 of the body includes a forward nose portion 16, which is fixed by a telescoping connection 18 to the main section of the forward half 10 of the body. The assembled halves of said body conveniently may be held pen-like in a human hand.

As illustrated, the forward nose portion 16 also includes means which receive, preferably by snap-action, a disposable predosed ampule syringe or cartridge 20 which comprises one form of receptical within which material to be delivered to a location of use is contained for discharge through a nozzle 22 which may be detachable or otherwise. As an alternative, it is to be understood that the invention is not to be restricted to the use of the ampule or cartridge 20; but may, in the forward nose portion 16 or otherwise, contain a compartment within which such material may be housed or contained for discharge through another type of nozzle means, not shown.

In the illustration shown in FIG. 1, the compartment comprising the ampule or cartridge 20 contains a piston 24, which in turn, is positioned to be engaged by the forward end of an elongated plunger rod 26, the rearward portion of which includes an upper rack of teeth 28 of a shape which may be the same as or different from the lower rack of teeth 30, as required, since these rows of teeth in the racks respectively serve different purposes as explained hereinafter. Especially as shown in the rearward half 12 of the body, illustrated in the lower portion of FIG. 1, the elongated plunger rod 26 terminates in a manually engageable rear portion 32 having a button 34 on the terminal end thereof. The plunger rod 26 also preferably is provided on at least one side with a longitudinal guide rib 31 slidable within a suitable complementary groove in the forward half 10 of the body to prevent rotation of the rod about its axis, as seen in FIG. 2.

Fixed between the plunger rod 26 and its manually engageable rear portion 32 is a transversely extending guide and abutment member 36, which is abutted by one end of pressure means comprising a coiled compression spring 38, which surrounds the manually engageable rear portion 32, and the other end of the spring abutts. the innermost end 40 of cylindrical cavity 42, which contains said spring. It will be observed that said spring is mounted in a manner to exert continual pressure upon the plunger rod 26 to urge or bias the same continually in feeding direction, in opposition to movement-stopping means now to be described. If desired, other equivalent pressure means may be used such as air or hydraulic pressure with suitable modifications.

Actuation of the elongated plunger rod 26 as well as the piston 24 occurs in a series of forward increments of movement, which may be termed feeding movement, and then stopping such movement after each increment of movement, such operation being automatically effected and controlled by a combination stop and release unit 42, which comprises a unitary block or member 44 extending transversely to the axis of the plunger rod 26 and having an internal opening 46 through which rod 26 extends. The member 44 has opposite parallel sides 48 which slidably move relative to the opposite side walls of a socket recess 50, best shown in FIG. 2, and the block 44 preferably having a vertical length, as viewed in FIG. 2, slightly greater than the depth of the socket recess 52 whereby, when the combination unit 42 and especially the block 44 thereof is fully depressed into the socket recess 52, as shown in FIG. 4 for example, the upper end 54 of block 44 will project a limited distance above the uppermost surface 56 of the forward half 10 of the body of the device.

Figure 3:
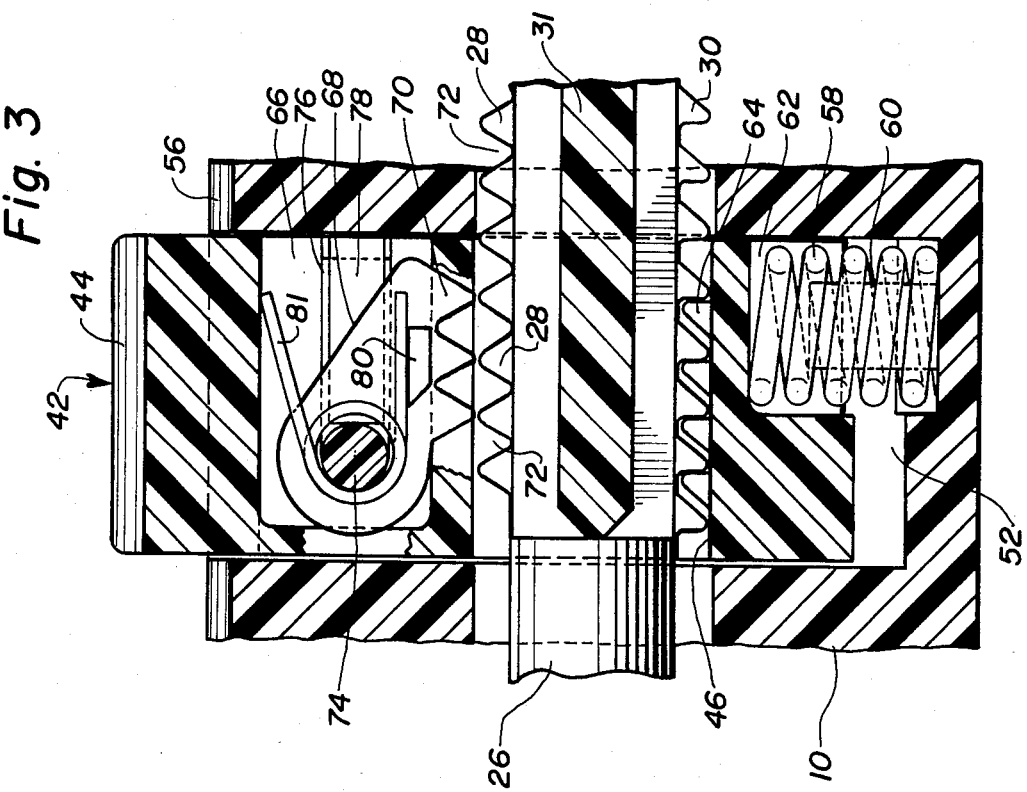
FIG. 3 is a fragmentary sectional view taken on the line 3—3 of FIG. 2, and showing the plunger in normally latched or stop position in its maximum retracted position.
Figure 2:
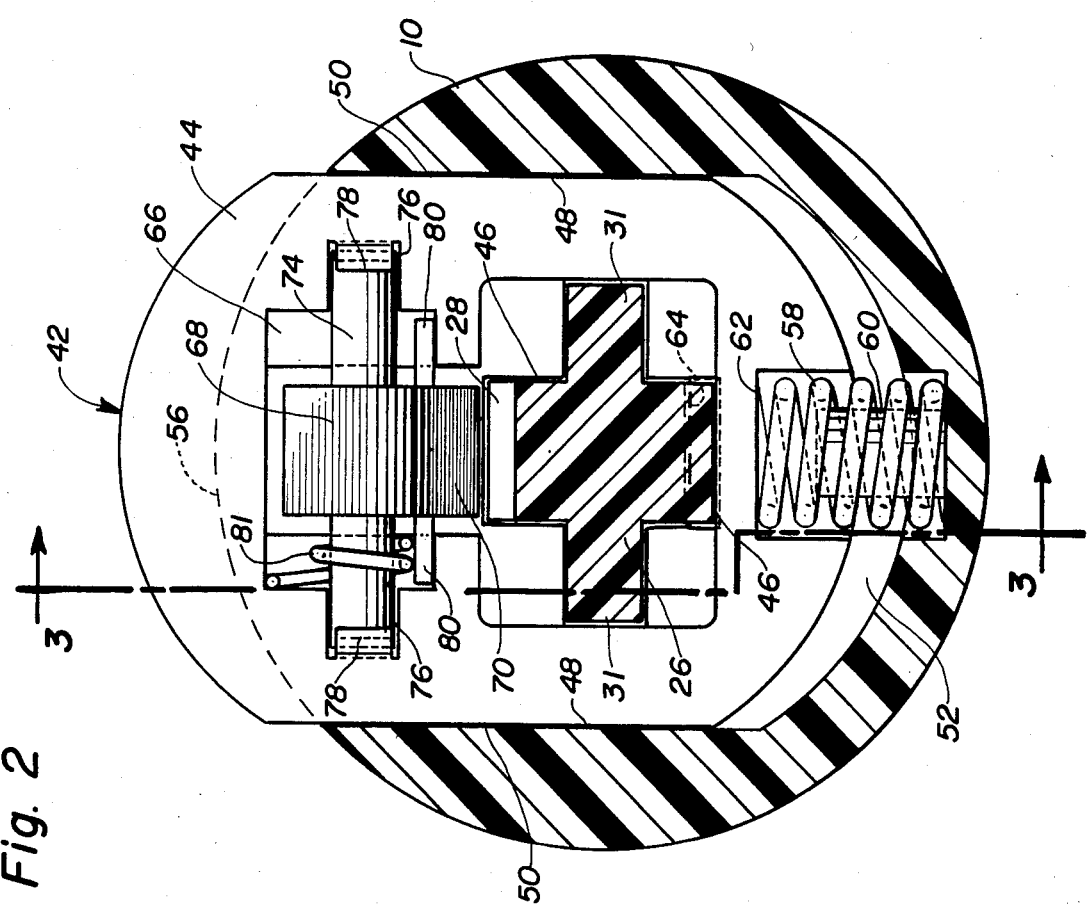
FIG. 2 is a transverse sectional view taken on the line 2—2 of FIG. 1, illustrating on a larger scale, than in FIG. 1, details of the actuating unit of the syringe comprising stop and release means.

In normal, starting position, which actually is the stop position of the plunger rod 26, the block 44 of the combination unit 42 is in the elevated position such as shown in FIGS. 2, 3 and 6. It is urged and maintained in this position by means of an additional compression spring 58 which, for example, is positioned by and surrounds a stud 60 molded integrally within the innermost portion of socket recess 52 as clearly shown in FIGS. 2-7. Preferably, the upper end of the spring 58 bears against the inner end of a socket 62 extending into the innermost end of block 44 of the combination unit 42.

Mounted upon the lower end of the internal opening 46 of block 44 are a series of so-called stop teeth 64 which are complementary to the teeth of the lower rack of teeth 30 of plunger rod 26 in that they co-engage and are both provided with abuting surfaces that are substantially transverse to the axis of the plunger rod 26, as best shown in FIGS. 3 and 6; hence, the reason for calling the same stop teeth 64. Such engagement occurs when the combination unit 42 is in the elevated position as shown in FIGS. 3 and 6 and the teeth 64 are sometimes referred to hereinafter and in the claims as "first teeth." The combination unit 42, when moved to depressed position as indicated by the upper direction arrow shown in FIGS. 4 and 7, effects movement of the plunger rod 26 and piston 24 when engaged by said rod by the following mechanism.

Referring to FIGS. 2–7, it will be seen that in the upper portion of block 44 of the combination unit 42 there is another recess 66 which contains a dog 68 having at least one tooth 70 thereon, but preferably has a plurality of similar teeth 70, which are complementary to the recesses 72 between the teeth 28 of the upper rack of teeth 28 on plunger rod 26, said tooth or teeth being hereinafter referred to as "second" tooth or teeth, the same operating in a manner so as to permit advancing increments of movement of the plunger rod 26 in the manner described below.

Dog 68 is supported upon a transverse pintle or axis 74 which, if desired, may be integrally molded with the dog 68 from suitable rigid plastic material, or otherwise, the ends of the pintle 74 being rotatably supported within complementary recesses 76 which, as best shown in FIG. 3, comprise slots 76 which are parallel to the plunger rod 26 and extend inward from one face of space 66 in the block 44 and, upon inserting the ends of the pintle 74 in said slots, said slots then are closed by frictionally inserting a rectangular block element 78 therein. Such blocks, best shown in FIGS. 2 and 3, are parallel and extending from opposite faces of the dog 68, are projections 80 and a biasing U-shaped spring 81 extends around the pintle 74 and opposite ends thereof respectively abut the upper surface of recess 76, as viewed in FIG. 3, and one of the ears 80.

The operation of dog 68 is as follows: Initially, when the device is in idle position, the combination unit 42 is in the elevated position such as shown in FIGS. 2, 3 and 6. In this position, the first teeth 64 of block 44 are in engagement with the rack teeth 30 in the lower side of plunger rod 26. When the block 44 is depressed, for example, to the positions shown in FIGS. 4, 5 and 7, the first teeth 64 are disengaged from the teeth 30 of the lower rack and when in this position, if desired, the plunger rod 26 may be manually moved in feeding direction until either the forward end of plunger rod 26 engages the piston 24 of ampule or cartridge 20 or, as mentioned above, if the forward end of the body has another form of compartment to contain the dispensible material, the plunger rod 26 preferably will be complementary to the inner walls of such compartment and thus engage material to be dispensed.

Such initial feeding movement of the plunger rod to engage either the piston or the material, as aforesaid, may occur by manually engaging the button 34 and moving the plunger rod in feeding direction. When the member 44 is depressed to release the first teeth 64 from engagement with the rack teeth 30, it will be seen from FIG. 4 that the so-called second teeth 70 on dog 68 are merely commencing to engage the teeth 28 on the uppermost rack of teeth and, under such circumstances, the plunger rod 26 is capable of being moved in feeding direction, as shown by the arrow on said member in FIG. 4, for a limited increment of distance sufficient to effect discharging a small amount of material from the forward end of the syringe.

As such forward movement of the piston rod 26 continues; however, the biasing spring 81 urges the dog 68 clockwise and the feeding movement of the plunger rod 26, which is caused by spring 38, actually effects such increment of feeding movement of the plunger rod and the so-called second teeth 70 ultimately fully mesh with the teeth 28 of the upper rack in somewhat of a camming action and, as shown in FIG. 5, finally stop any further feeding movement of plunger rod 26. Thus, by sequentially depressing the block 44 to actuate the combination unit 42 and then releasing the same, increments of feeding movement of the plunger rod 26 are effected until the desired amount of material has been discharged from the nozzle 22 or other discharge means at the forward end of the device in a manner in which the material is readily visibly seen by the operator for accurate placement.

When it is desired to move the plunger rod 26 in retracting position, this is readily accomplished by depressing the block 44 to disengage the teeth 64 on the block from the rack teeth 30 on the lower side of piston rod 26. Withdrawal movement, as visualized in FIG. 7, in connection with the direction arrows on the right-hand side thereof, easily is effected by cammingly moving the upper rack teeth 28 with respect to the second teeth 70 on dog 68 against the action of the biasing spring 80.

It is also contemplated within the purview of the present invention, that especially if the plunger rod 26 is in its outer most extended position, such as that illustrated in FIG. 1, wherein the forward end of the plunger rod may be spaced a substantial distance from the piston 24, for example, or its equivalent means in other construction described hereinabove; initial movement of the plunger rod in feeding direction until it engages piston 24 or otherwise, may be effected by limited modification of the device. For example, by only partially depressing the block 44 against the action of the spring 58 sufficiently to barely disengage the stop teeth 64 from the rack teeth 30 on the plunger rod and then forceably pushing upon the button 34 to moe the piston rod 26 in feeding direction against the operation of second teeth 70 on the dog 68, somewhat in camming manner or otherwise; this may be made possible, for example, by suitable angulation of the respective teeth 70 and 28, and particularly when the teeth 70 are not fully meshed with the teeth 28 of the rack thereof.

Thereafter, forward advance movement of the plunger rod 26 is effected by successively depressing block 44 and manually releasing the same to produce the aforementioned increments of movement of the plunger rod in feeding direction and thereby dispense a desired amount of material from nozzle means at the forward end of the device. The above-described operation of teeth 70 relative to rack teeth 28 is made so as not to require the tedious initial advance movement of the plunger rod 26 toward the piston 24 by such successive depressings and releasings of the block 44 until the forward end of rod 26 engages piston 24 or otherwise.

From the foregoing, it will be seen that the present invention provides a relatively simple multiple dosage syringe readily operated by successively manually depressing and releasing the combination stop and release member 42, comprising block 44, while comfortably and conveniently holding the device in the hand of the operator pen-like and no additional manipulation of the plunger rod 26 is required to effect such stepwise feeding. The mechanism employed to effect such feeding movement is far more simple than the presently used syringes capable of effecting successive movements of the plunger rod thereof, whereby the present invention constitutes a meritorious advance over the prior art. Further, substantially all components of the syringe may be manufactured precisely by molding from plastic or similar rigid material, thereby minimizing the cost of production.

The foregoing description illustrates preferred embodiments of the invention. However, concepts employed may, based upon such description, be employed in other embodiments without departing from the scope of the invention. Accordingly, the following claims are intended to protect the invention broadly, as well as in the specific forms shown herein.

We claim:

1. A multiple dosage device including in combination an elongated body including a compartment for material to be dispensed, a piston operable in said compartment to engage the material in opposition to a discharge nozzle on said body, a plunger rod in said body operable to engage said piston, pressure means in said body operable constantly against said plunger rod to urge it in a direction to effect discharge of said material from said compartment, elongated racks of teeth respectively on opposite edges of said plunger rod, and a manually-operable stop and release unit movable transversely to said plunger rod between projected and retracted positions and operable in sequence relative to said plunger rod, said unit having a unitary member encircling said plunger rod and including first teeth movable into engagement with the teeth on one of said racks to stop movement of said rod by said pressure means when said unit is in projected position and said unit having a second tooth pivotably carried by said member in opposition to said first teeth and movable relative to said member camlike relative to the opposite rack of teeth on said rod when said unit is depressed from a projected position to permit said pressure means to move said rod in feeding direction a limited predetermined distance which is limited by said second tooth fully meshing with said opposite rack of teeth in a manner to stop feeding movement of said rod until said unit next is operated to effect such feeding movement of said piston by said pressure means.

2. The device according to claim 1 in which said second tooth of said unit is formed on a dog pivotally mounted within said member, and further including a spring positioned in said member and positioned to act upon said dog and bias said second tooth in limited pivotal camlike manner from a spaced position relative to the teeth of said opposite rack into full meshing engagement with said opposite rack of teeth on said rod, and said pivotal movement of said dog and tooth being arranged to permit feeding movement of said rod said limited distance before said rod is stopped by said full meshing engagement of said tooth and opposite rack on said rod.

3. The device according to claim 1 in which said unitary member is of limited thickness and is positioned within a socket recess of complementary size in said body intermediately of the ends thereof for limited reciprocating movement between a substantially fully depressed position and an elevated position in which the outer end of said member projects a limited distance above the surrounding exterior surface of said body; said unitary member having a transverse opening through which said plunger rod extends for engagement with said piston, and additional spring means mounted within the innermost end of said socket recess for engagement with the inner end of said member and operable constantly to bias said member toward the elevated position thereof.

4. The device according to claim 3 in which said piston rod is generally rectangular in cross-section and is provided with said rack teeth respectively along the upper and lower edges thereof, and said opening in said unitary member having said first teeth formed on the lower side of said opening for engagement with the lower rack teeth and the portion of said unitary member above said opening having a recess in which said dog with said second tooth is mounted thereon for limited pivotal movement from a position of nonengagement with said upper rack of teeth to a position in which said tooth is fully meshed between the teeth of said upper rack to stop feed movement of said piston rod after permitting said feed movement of said rod to function to discharge a metered amount of material.

* * * * *